United States Patent
Kong

Patent Number: 5,935,483
Date of Patent: Aug. 10, 1999

[54] MULTI-PURPOSE MINERAL POWDER AND ITS PROCESS

[75] Inventor: Byung-Suk Kong, Pusan-si, Rep. of Korea

[73] Assignee: Yong-Mi Kim, Pusan-si, Rep. of Korea

[21] Appl. No.: 08/846,508

[22] Filed: Apr. 29, 1997

[51] Int. Cl.$^6$ ............................ A61K 33/12; A61K 33/14
[52] U.S. Cl. ............................ 252/1; 424/650; 424/680; 501/73; 501/113; 501/121
[58] Field of Search .................... 252/1; 424/650, 424/680, 683, 684; 501/73, 113, 118, 121

[56] References Cited

U.S. PATENT DOCUMENTS

| | | | |
|---|---|---|---|
| 4,376,709 | 3/1983 | Johnson et al. | 252/1 |
| 4,477,580 | 10/1984 | Fleming | 501/73 |
| 5,597,550 | 1/1997 | Mo | 424/650 |

OTHER PUBLICATIONS

"Piopower Rare Materials", Korea Ore Research Institute, Dec. 10, 1996, pp. 1–20.

"Espino Rare Materials", Korea Ore Research Institute, Dec. 10, 1996, pp. 1–20.

*Primary Examiner*—George Wyszomierski
*Attorney, Agent, or Firm*—Skjerven, Morrill, MacPherson, Franklin & Friel LLP

[57] ABSTRACT

The present invention relates to multi-purpose mineral powder emitting the large quantities of far infrared rays, negative ion and oxygen heat having ingredients of germanium of 20 weight percent, clinochlore of 10 weight percent, jade of 10 weight percent, zeolite of 10 weight percent and halite of 50 weight percent, and its process, in which the above five ingredients are pulverized to about 300 mesh; are placed into an inner surface having silver leaf (Ag) of an internal furnace made of chondrodite; are heated through a heating plate for nine days at about 1000° C. so as to have thermal deformation after placing chondrodite pulverized to about 200 mesh between the inner surface of the electric heating plate and the outer surface of the internal furnace; and are then pulverized to about 325 mesh.

3 Claims, 5 Drawing Sheets

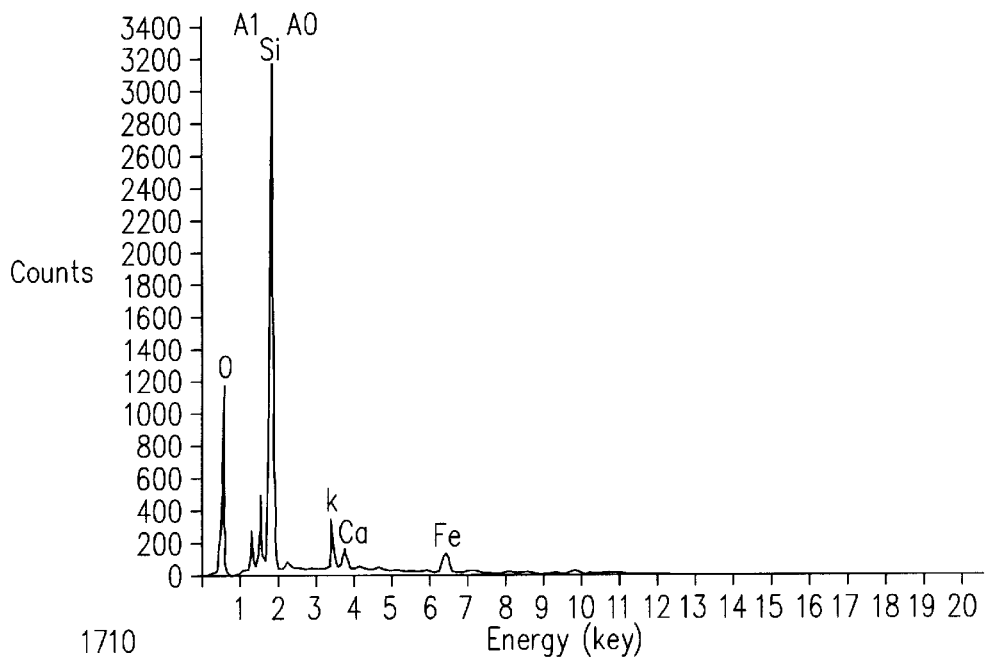
FIG. 3 SEM-EDX Spectrum of the Requested Specimen
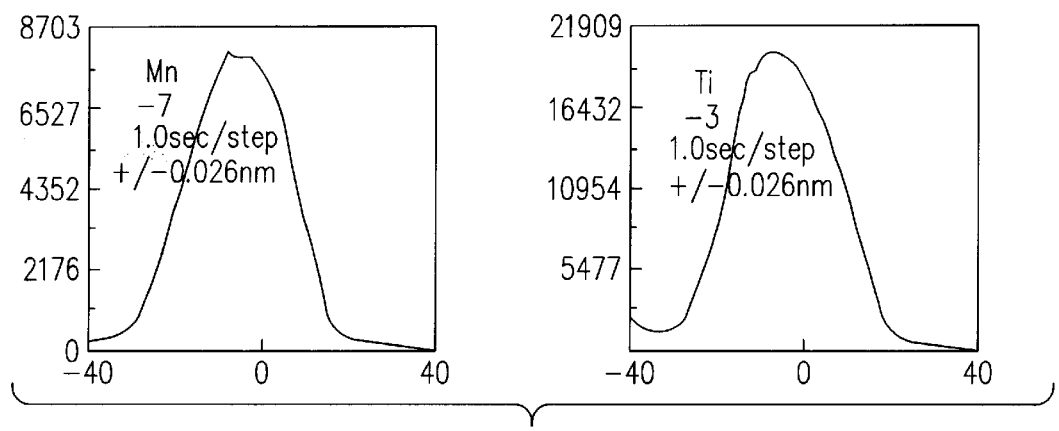
FIG. 4 ICP Profile of the Requested Specimen

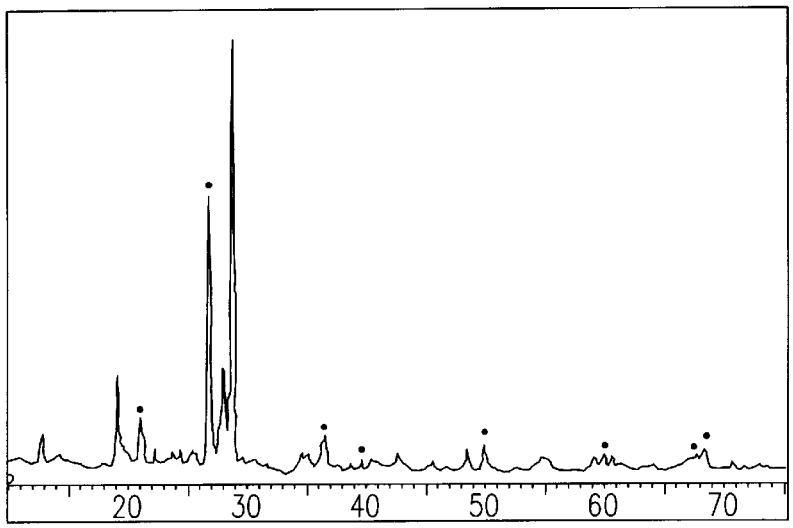

D/MAX-B          PEAK FINDING PROGRAM                    V1.8
===========================================================

DATA FILE:  C:\DATA\Z00099.RAW
COLLECTED ON 23-MAR-96    AT 16:59:55
SAMPLE IDENTIFICATION:                    TK 4710
DATE OF-PEAK SEARCH:                      3-34-96 AT 11:25:49

START 2THETA:   10.000           STOP 2THETA:    75.000
STEP SIZE:       0.050           SCAN SPEED:     10.000
KV:   40.    MA:  50

PEAK FINDING PARAMETERS

THRESHOLD VALUES :   5.0, 10.0
        RELATIVE CUTOFF INTENSITY :   0.0
  TYPICAL FULL WIDTH-HALF MAXIMUM :   0.20
  MINIMUM FULL WIDTH-HALF MAXIMUM :   0.08
                      PEAK SPAN :   15

XRD Spectrum of the Requested Specimen (*SiO$_2$ peak)

FIG. 5A

| FIG. 5A |
|---|
| FIG. 5B |

KEY TO FIG. 5

```
BACKGROUND-SUBTRACTED DATA WILL BE IN FILE C:\DATA\Z00099.BSD
      PEAKS DATA WILL BE IN THE NEW FILE C:\DATA\Z00099.PKS
         THRESHOLD DATA WILL BE IN FILE C:\DATA\Z00099.THD
```

| PEAK | 2-THETA | D-SPACE | I(REL) | I(CPS) | FWHM |
|---|---|---|---|---|---|
| 1 | 12.450 | 7.1039 | 8.52 | 119.3 | 0.243 |
| 2 | 18.900 | 4.6916 | 20.30 | 284.4 | 0.196 |
| 3 | 19.350 | 4.5835 | 5.37 | 75.2 | 0.394 |
| 4 | 20.800 | 4.2671 | 14.36 | 201.2 | 0.187 |
| 5 | 21.950 | 4.0461 | 6.29 | 88.1 | 0.290 |
| 6 | 23.500 | 3.7826 | 5.09 | 71.3 | 1.288 |
| 7 | 24.150 | 3.6823 | 4.75 | 66.6 | 0.589 |
| 8 | 25.100 | 3.5450 | 4.68 | 65.6 | 0.638 |
| 9 | 26.600 | 3.3484 | 72.75 | 1019.3 | 0.177 |
| 10 | 27.450 | 3.2466 | 11.26 | 157.8 | 0.239 |
| 11 | 27.850 | 3.2009 | 20.06 | 281.0 | 0.283 |
| 12 | 28.550 | 3.1240 | 100.00 | 1401.1 | 0.218 |
| 13 | 34.400 | 2.6049 | 4.47 | 62.7 | 0.433 |
| 14 | 36.100 | 2.4861 | 5.78 | 80.9 | 0.640 |
| 15 | 36.500 | 2.4597 | 7.95 | 111.3 | 0.787 |
| 16 | 39.400 | 2.2851 | 3.25 | 45.6 | 0.230 |
| 17 | 40.250 | 2.2388 | 3.79 | 53.2 | 0.448 |
| 18 | 42.400 | 2.1301 | 4.88 | 68.3 | 0.331 |
| 19 | 42.750 | 2.1135 | 2.68 | 37.6 | 0.640 |
| 20 | 48.600 | 1.8719 | 6.05 | 84.7 | 0.229 |
| 21 | 50.100 | 1.8193 | 3.57 | 120.1 | 0.179 |
| 22 | 54.800 | 1.6738 | 3.63 | 50.9 | 0.372 |
| 23 | 54.950 | 1.6696 | 2.78 | 38.9 | 0.242 |
| 24 | 59.900 | 1.5429 | 5.76 | 80.7 | 0.177 |
| 25 | 60.550 | 1.5279 | 4.04 | 56.6 | 0.319 |
| 26 | 67.650 | 1.3838 | 2.33 | 32.6 | 0.689 |
| 27 | 68.100 | 1.3757 | 3.39 | 47.5 | 0.431 |
| 28 | 68.300 | 1.3722 | 3.39 | 47.5 | 0.297 |

XRD Spectrum of the Requested Specimen (*$SiO_2$ peak)

FIG. 5B

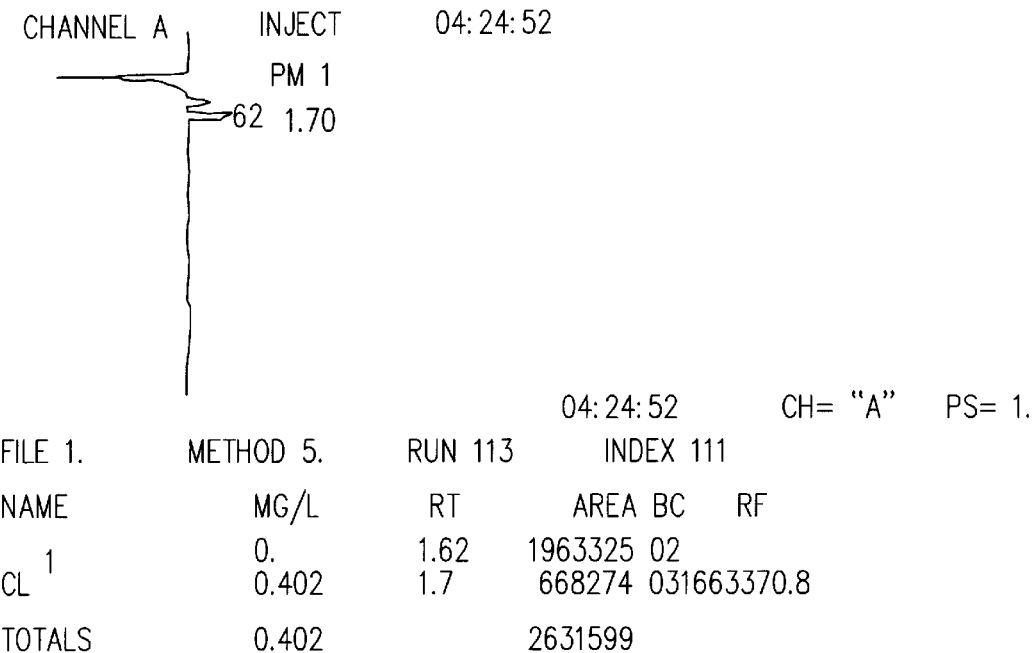
FIG. 6 Ion Chromatograph of Macro Solution
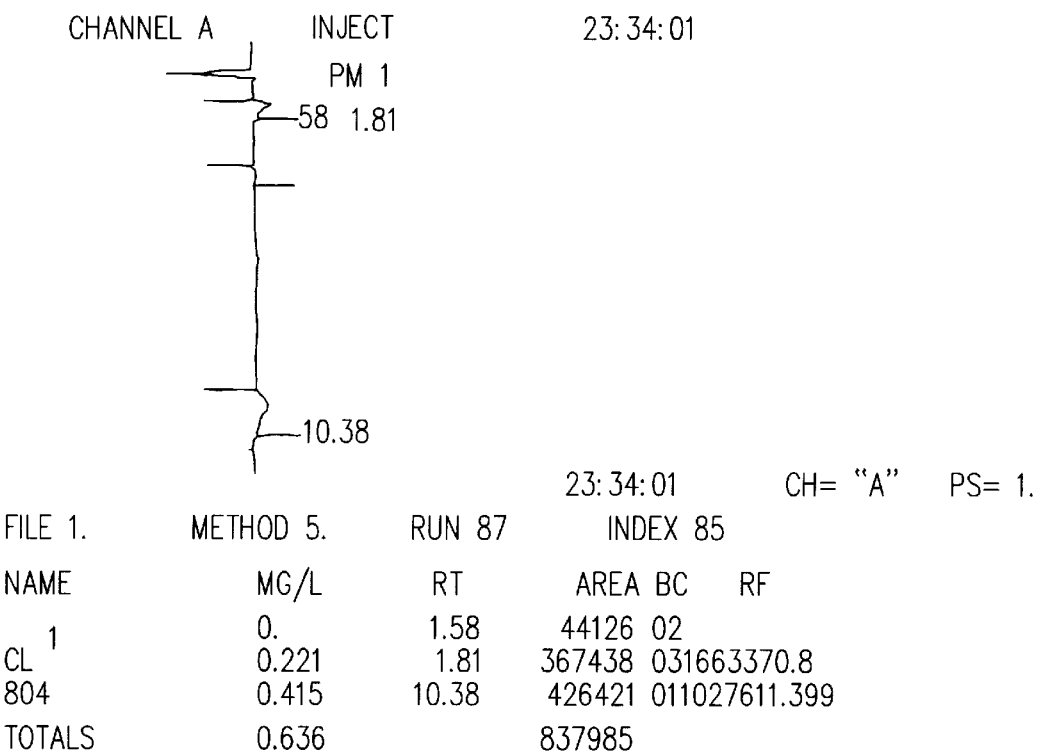
FIG. 7 Ion Chromatograph of Specimen (Liquated Solution)

MULTI-PURPOSE MINERAL POWDER AND ITS PROCESS

BACKGROUND OF THE INVENTION

1. Field of the Invention

The present invention relates to multi-purpose mineral powder emitting large quantities of far infrared rays, negative ion and oxygen heat and its process.

2. Description of the Related Art

The space of the earth on which we live is the space which terrestrial magnetism extends to. The earth is originally a giant mineral magnet. The earth is one of the nine great planets in the solar system.

The sun emits light and heat, and also emits solar energy. This energy has the wavelength of six million meters and is called the energy of the longest wavelength. The solar magnetism endlessly directs onto the earth and thus had the earth become a great magnet. The earth is able to emit earth magnetism (energy). All of the solar energy and the earth magnetism form natural magnetism. Sufficient covering of our life space maintains and protects our health, and enables all life to grow up well and to endlessly maintain their vigorous live. If, one day, the earth magnetism (energy) suddenly were to vanish, all the creatures would perish.

Natural earth magnetism (energy) is very important but considerably rare. Accordingly, it is sufficient for healthy persons but greatly insufficient for enfeebled persons. For these reasons, by selecting several kinds of ores, semi-precious stones having energy and making a powder by a process in a special furnace (burning pot), a mineral powder is formed for emitting far infrared rays, negative ions and oxygen heat.

The natural earth magnetism in the resultant powder emits far infrared rays, negative ions and oxygen. In general, infrared rays refer to electromagnetic waves having a wavelength range of 0.76–1000 micron ($\mu$). Near infrared rays have the wavelength of 0.76–1.5 micron, intermediate infrared rays have the wavelength of 1.5–5.6 micron and far infrared rays have the wavelength 5.6–1000 micron (Far Infrared Business published by Sunmark on December 25, 1988).

Far infrared rays are used for various purposes such as heating, drying, ripening, nurturing and alleviation of pain. It is also known that application of the far infrared rays to the human body provides the perspiration operation which secretes lots of sweat and alieves pain. In addition, since the announcement of a clinical test which reveals good effects for the biological rhythm of the human body, there are many trials for using far infrared rays desirably in the health industry or the food industry ("Theory and Practice for Heating of Far Infrared Rays" pp. 226–239 by Far Infrared Rays Committee of Japan Electric Heat). As a consequence, a variety of goods using the far infrared rays are produced in large quantities and sold in the market. For example, a sauna using far infrared rays can improve the perspiration operation of the human body with the lower temperature than that of a steam sauna.

In the case of a steam sauna, steam of high temperature (about 70–80° C.) is supplied in a sauna room, and thus users are unable to endure for a long time within the sauna room. However, the far infrared rays sauna has a higher perspiration operation than that of the steam sauna, even with a sauna temperature of about 40° C. This explains the phenomena that far infrared rays are absorbed in the human body and a self-generated heating is caused by means of a resonance operation of water particles within the human body.

It is a known fact that negative ion is opposite to positive ion. Mr. Bert Sakmann and Mr. E. Necher studied together and formulated a theory which subsequently won the prize for Nobel Physiology and Medical Science Award in 1991. The theory reveals that a disease structure in the human body can be detected through the movement of negative ions within the cell. In the event that the human body has more positive ion due to external or internal effects, interest concerning adding negative ion to compensate for the depleted negative ion, by using food or a life environmental device is at a high level.

Applying a negative ion to the human body having more positive ion is known in an autonomic nerve adjusting operation, a purification operation of the blood, a cell revival operation and in a resistance improvement operation of the cell effect.

Various ions in the atmosphere vary according to the weather conditions. When a low atmospheric pressure such as a line of discontinuity and a cold front passes, positive ion increases, and with these effects, negative ion within the human body decreases and the positive ion increases thereby the occurrence rate of a disease such a neuralgia, cerebral apoplexy and asthma increases.

A conventional product emitting far infrared rays is a material sold under the brand name "BIO CERAMIC." In such product, the specific functions such as the antibacterial effects, prevention of decoloration, deodorization, etc., are maximized by mixing mineral matter having the specific function to a ceramic material or applying a chemical substance thereto. The product is supplied in the form of powder, particle or liquid phase.

However, the conventional far infrared rays-emitting material (product) had a drawback of emitting insufficient far infrared rays. Also, as such material may contain various chemical substances, users who need to avoid those chemical substances cannot use the material as a cosmetic.

An ore normally emits oxygen heat, especially a semi-jewel ore according to the present invention emits the large quantity of oxygen heat. For example, in connection with roasting of meat or cooking of rice in a stone pot, the fact that the roasted meat becomes tender or the boiled rice is delicious and remains unchanged for a long time is due to the oxygen heat emitting from the ore.

The human body consists of about 70–100 trillion cells each of which is measured in the unit of the micron ($\mu$), one thousandth of 1 mm. The thickness of the cell is measured in the unit of micron but some of the cells are very long. Namely, a muscular cell normally has a length of 1–40 mm and a cell in the inguinal region has a length of 30 mm. Some nerve cells have a length of 2 m. The cells of the human body also have an infinite variety of figures. A skin cell is broad and plain like a brick but a nerve skin is thin and long like a thread. A red blood cell has a cut-out shape in the middle like a doughnut and a white corpuscle has no definite shape. Such various cells may increase their numbers and may be changed into the cells having various shapes and functions. Applying heat to the mineral powder results in oxygen heat which emits to cells of the human body. That is, a large quantity of the mysterious natural oxygen heat which is salutable for the human body is emitted to the cell of the human body so that the cell can be energetically activated.

SUMMARY OF THE INVENTION

An object of the present invention is to provide multi-purpose mineral powder comprising only natural minerals entirely excluding chemical substances which powder emits a large quantity of negative ion, far infrared rays and oxygen heat.

BRIEF DESCRIPTION OF THE DRAWINGS

FIG. 3 is a graph of the SEM-EDX spectrum.

FIG. 4 is a graph of the ICP profile.

FIG. 5 is a graph of the XRD spectrum.

FIG. 6 is a graph of an Ion chromatograph of macro-solution.

FIG. 7 is a graph of an Ion chromatograph of liquated solution.

DETAILED DESCRIPTION OF THE PREFERRED EMBODIMENT

Hereinafter, desirable examples of the present invention will be described with reference to the accompanying drawings.

Figure 1:
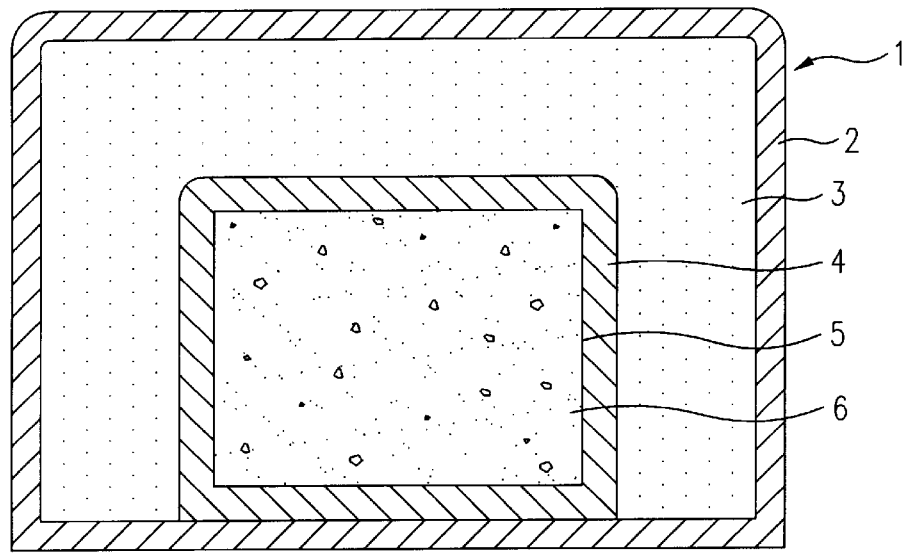
FIG. 1 is a schematic view illustrating a furnace for manufacturing multi-purpose mineral powder according to the present invention.

Referring to FIG. 1, a furnace 1 for manufacturing multi-purpose mineral powder according to the present invention comprises an electric heating plate 2, an internal furnace 4 and an internal inside wall 5 of the furnace is coated with silver (Ag). The electric heating plate 2 is heated with gas or the other fuel. The internal furnace 4 is made of chondrodite. A mixture of germanium of 20 weight percent, clinochore of 10 weight percent, jade of 10 weight percent, zeolite of 10 weight percent and halite of 50 weight percent is pulverized to about 300 mesh by using a normal pulverizer and placed in the furnace. Reference numeral "6" represents the mixed powder of the aforesaid ores.

After placing chondrodite 3, pulverized to about 200 mesh between the inner surface of the electric heating plate 2 and the external surface of the internal furnace 4, the chondrodite is heated through the electric heating plate 2 for nine days at about 1000° C. The chondrodite is heated at the initial temperature of 1000° C. and due to self-combustion heat during the heating the temperature rises up to about 1500° C. Such an intense heat causes thermal deformation to the five kinds of mineral ingredients within the internal furnace 4 and, consequently, heavy metals harmful to the human body are burnt out. The ingredients are then in a lump-form having more than twenty kinds of natural minerals and 36 other kinds of minerals found in normal ores, as shown in Table 1. After the chrondrodite is burnt, a slow cooling is conducted.

Figure 2:
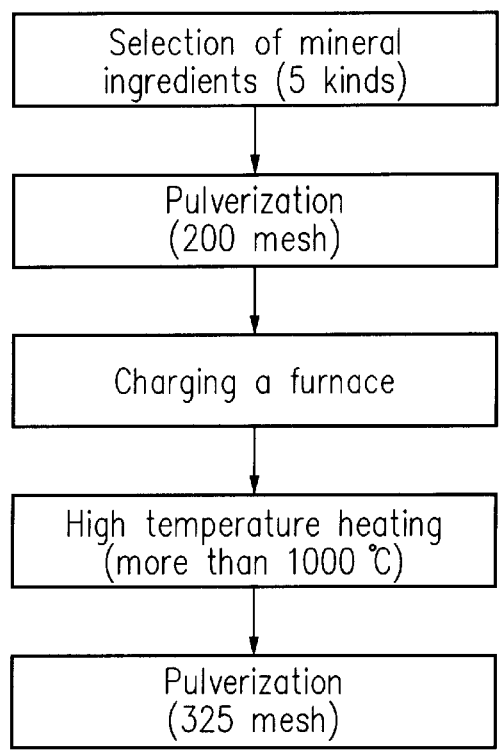
FIG. 2 is a block diagram illustrating the manufacturing of the multi-purpose mineral powder according to the present invention.

As shown in FIG. 2, such lump is pulverized to a fineness of about 325 mesh.

TABLE 1

| Item for test | Unit | Result value | Test method |
| --- | --- | --- | --- |
| Qualitative test | | Main ingredient: $SiO_2$, accessory ingredient: Al, Mg and the small quantity of Ca, Fe, K, Mn, Na, Ti were detected | SEM, EDX, ICP, XRD |
| Quantitative test | % | $Al_2O_3$ 8.37<br>CaO 1.45<br>$Fe_2O_3$ 2.20<br>$K_2O$ 4.33<br>MgO 14.8 | KSL 3128-94 |
| | | MnO 0.06<br>$Na_2O$ 1.76<br>$TiO_2$ 0.25<br>$SiO_2$ 63.1<br>Ignition loss 3.58 | |
| Liquation test | $SO_4^{2-}$ ppm | 16.6 | KSM 0035-93 (Liquation condition: Specimen 5 g × deionic water 200 ml × 200 rpm × normal temperature × 2 hrs) |
| | Cl— ppm | Not detected | |
| | Br— ppm | Not detected | |
| | NO2— ppm | Not detected | |
| | $PO_4^{3-}$ ppm | Not detected | |
| | F— ppm | 5.8 | *(below) |

*KSM 0036-93, Liquation condition: specimen 9.02 g X deionic water 100 ml × 200 rpm × normal temperature × 2 hrs The ingredients of mineral powder according to the present invention are as described in Table 1, and are in accordance with a data report concerning the results of tests conducted by the Korea Testing and Research Institute for Chemical Industry, hereinafter called the "Institute."

Such ingredients described in Table 1 emit large quantities of infrared rays, negative ion and oxygen heat salutable for the human body.

The ingredients of mineral powder according to the present invention has more than 99.0% of far infrared rays radiation ratio having the wavelength of 8–14 micron at 37° C. and emits more than six hundred thousand number of negative ion per 1 kg of the ingredient. The calorific value of oxygen is 56 Kcal. With reference to the method of examination herein, the far infrared rays were measured by applying KS.A 5302-91. Negative ion was measured by applying Negative Ion Measuring Equipment Model NO. MDK-01C of a Company, Messrs. Schomandl in Germany and the calorific value of oxygen was measured by applying KS.E 3707-90. The aforesaid mineral power has the pH of 7.4–7.9.

A quantitative analysis and qualitative analysis of a mineral specimen was performed by the Institute.

For the qulitative analysis the following test devices were employed:

SEM (Stereoscan 440, Leica, England)

EDX (Voyager, Noran, USA)

ICP (Labtam 8440, Australia)

XRD (D/MAX, Australia)

The test method was: After drying the specimen, it was powdered and its main ingredients were analyzed with the SEM-EDX equipment and a structural analysis conducted with a XRD device. After melting the powder specimen with a flux, the specimen was dissolved with hydrochloric acid and the qualitative analysis for the small quantity elements was conducted with the ICP device.

The test results were: The main ingredient is SiO2, and the accessory ingredients are Al and Mg. Small quantities of Ca, Fe, K, Mn, Na, Ti were detected (Refer to FIGS. 3 to 5). FIG. 3 shows the SEM-EDX spectrum, FIG. 4 shows ICP profile and FIG. 5 shows the XRD spectrum.

For the quantitative analysis an ICP (Laptam 8440, Australia) test device was employed and a test method and analysis conducted in accordance with KSL 3128-94.

The test results on the specimen are seen in Table 2.

TABLE 2

|  | Item for Test | Unit | Result Value |
|---|---|---|---|
| Quantitative Analysis | $Al_2O_3$ | % | 8.37 |
|  | CaO |  | 1.45 |
|  | $Fe_2O_3$ |  | 2.20 |
|  | $K_2O$ |  | 4.33 |
|  | MgO |  | 14.8 |
|  | MnO |  | 0.06 |
|  | $Na_2O$ |  | 1.76 |
|  | $TiO_2$ |  | 0.25 |
|  | $SiO_2$ |  | 63.1 |
|  | Ignition loss |  | 3.58 |

An analysis for negative ion of $SO_4^{2-}$ was performed using an Ion Chromatography (Dionex 4000I, USA) test device.

The test device operational conditions were:

Eluen; 1.8mM $Na_2CO_3$, 1.75mM Na $HCO_3$

Regenerate; 0.025N $H_2SO_4$

Flow rate; 2.0 ml/min

Detector; Suppressed conductivity (at 30 μs)

The test method was as follows:

After adding a fixed quantity of the specimen to a fixed quantity of deionic water, it was liquated out with a shaker of 200 rpm at normal temperature for two hours and then, "F" was analyzed in accordance with KSM 0036-93 and the residual negative ion was analyzed in accordance with KSM—0035-93. The test results are seen in Table 3:

TABLE 3

|  | Item tor test | Unit | Result value |
|---|---|---|---|
| Liquation test | $SO_4^{2-}$ | ppm | 16.6 |
|  | $Cl^-$ |  | Not detected |
|  | $Br^-$ |  | Not detected |
|  | $NO_3^-$ |  | Not detected |
|  | $PO_4^{3-}$ |  | Not detected |
|  | $F^-$ |  | 5.8 |

FIG. 6 graphically shows the ion chromatograph of the micro solution while FIG. 7 graphically shows the ion chromatograph of a liquated solution.

The general result for the testing are seen Table 4.

TABLE 4

|  | Item for test | Unit | Result value |
|---|---|---|---|
| Quantitative test |  | — | Main ingredient: SiO2, accessory ingredient: Al, Mg, and small quantity of Ca, Fe, K, Mn, Na, Ti were detected. |
| Quantitative test | $Al_2O_3$ | % | 8.37 |
|  | CaO |  | 1.45 |
|  | $Fe_2O_3$ |  | 2.20 |
|  | $K_2O$ |  | 4.33 |
|  | MgO |  | 14.8 |
|  | MnO |  | 0.06 |
|  | $Na_2O$ |  | 1.76 |
|  | $TiO_2$ |  | 0.25 |
|  | $SiO_2$ |  | 63.1 |
|  | Ignition loss |  | 3.58 |
| Liquation test | $SO_4^{2-}$ | ppm | 16.6 |
|  | $Cl^-$ |  | Not detected |
|  | $Br^-$ |  | Not detected |
|  | $NO_3^-$ |  | Not detected |
|  | $PO_4^{3-}$ |  | Not detected |
|  | $F^-$ |  | 5.8 |

As the result of the XRD analysis, the main ingredient of the requested test specimen is $SiO_2$. Al, Mg, Fe, etc. were detected. The content of these elements was based on the oxide of the element. As the result of the composition analysis for the test specimen, the specimen ingredients were $SiO_2$ of 63.1%, $Al_2O_3$ of 8.37%, CaO of 1.45%, $Fe_2O_3$ of 2.20%, $K_2O$ of 4.33%, MgO of 14.8%, MnO of 0.06%, $Na_2O$ of 1.76%, $TiO_2$ of 0.25%, and the ignition loss was 3.58%. As the result of liquation test, $So_4^{2-}$ was 16.6 ppm and F– was 5.8 ppm, $PO_4^{3-}$ was not detected.

Multi-purpose mineral powder according to the present invention is a combination of mineral matter emitting a large quantity of far infrared rays, negative ion and oxygen heat. It is the useful invention applicable to foods, petroleum, cosmetics, architectural material, electronic products, wall paper, physical treatment device, medicines, plastic, glass, steel, motor car parts, health care houses, soap, health care goods, medical devices, health care fibers, various heating devices, tools and paint.

What is claimed is:

1. Multi-purpose mineral powder capable of emitting a large quantity of far infrared rays, negative ion and oxygen heat, the powder comprising ingredients of germanium of 20 weight percent, clinochlore of 10 weight percent, jade of 10 weight percent, zeolite of 10 weight percent and halite of 50 weight percent, wherein said powder has been produced by a process comprising:

pulverizing said ingredients to about 300 mesh;

placing the pulverized ingredients into a chondrodite internal furnace having a silver coated inner surface;

heating the pulverized ingredients for nine days at about 1000° C. so as to thermally deform said ingredients; and pulverizing the thermally deformed ingredients to about 325 mesh.

2. The mineral powder of claim 1, wherein said ingredients are heated by an electric heating plate disposed around said internal furnace.

3. The mineral powder of Claim 2, wherein chondrodite is disposed between an inner surface of said electric heating plate and an outer surface of said internal furnace.

* * * * *